(12) United States Patent
Roldan Carrillo et al.

(10) Patent No.: US 8,895,479 B2
(45) Date of Patent: *Nov. 25, 2014

(54) HEAVY OIL RECOVERY PROCESS USING EXTREMOPHILE ANAEROBIC INDIGENOUS MICROORGANISMS

(75) Inventors: Teresa Guadalupe Roldan Carrillo, Mexico City (MX); Gladys Teresa Castorena Cortés, Mexico City (MX); Norma Icoquih Zapata Peñasco, Mexico City (MX); Romeo Jesús Reyes Ávila, Mexico City (MX); Andrés Moctezuma Berthier, Mexico City (MX); Patricia Olguín Lora, Mexico City (MX)

(73) Assignee: Instituto Mexicano del Petroleo, Mexico City (MX)

( * ) Notice: Subject to any disclaimer, the term of this patent is extended or adjusted under 35 U.S.C. 154(b) by 320 days.

This patent is subject to a terminal disclaimer.

(21) Appl. No.: 13/293,802

(22) Filed: Nov. 10, 2011

(65) Prior Publication Data

US 2012/0122740 A1 May 17, 2012

(30) Foreign Application Priority Data

Nov. 12, 2010 (MX) .................... MX/a/2010/012349

(51) Int. Cl.
*C09K 8/60* (2006.01)
*C09K 8/582* (2006.01)
*C12N 1/20* (2006.01)

(52) U.S. Cl.
CPC .. *C09K 8/582* (2013.01); *C12N 1/20* (2013.01)
USPC ....................................................... 507/201

(58) Field of Classification Search
CPC ............ C09K 8/58; C09K 8/584; C09K 8/12; C09K 8/588; C09K 8/62; C09K 2208/10; C09K 8/032; C09K 8/035; C09K 8/24; C09K 8/42; C09K 8/487; C09K 8/50; C09K 8/512; C09K 8/56; C09K 8/5758; C09K 8/68; C09K 8/34; C09K 8/467; C09K 8/536; C09K 8/60; C09K 8/605; C09K 8/80; C09K 8/805; C12N 9/0006; C12N 15/52; C12N 9/2434; C12N 9/2437; C12N 9/88; C12N 15/81; C12N 9/90; C12N 15/70; C12N 9/0008; C12N 9/1029; C12N 15/74; C12N 1/20; C12N 9/242; C12N 11/14; C12N 1/18
See application file for complete search history.

(56) References Cited

U.S. PATENT DOCUMENTS 3,185,216 A * 5/1965 Hitzman ....................... 166/246
7,484,560 B2 2/2009 Lal et al.
8,631,865 B2 * 1/2014 Olguin Lora et al. ......... 166/246
2007/0092930 A1 * 4/2007 Lal et al. .......................... 435/41
2007/0181300 A1 8/2007 Busche et al.

FOREIGN PATENT DOCUMENTS

| CN | 101699025 | * | 4/2010 |
| WO | 2009/001098 | | 12/2008 |
| WO | 2009/009382 | | 1/2009 |

OTHER PUBLICATIONS

T. F. Yen, J. K. Park, K. Lee, Y. Li, Ch. R-19 fate of surfactant vesicles surviving from thermophilic, halotolerant, spore forming, *Clostridium thermohydrosulfuricum*, Development in petroleum Science, 1991, 31, 297-309.*
J. Enas, E. Sogaard, The Utilization of *Thermoanaerobacter brockii* Subsp. Lactietylicus Strain 9801 for Microbial Enhanced Recovery, ISMOS2 Abstarct Book, Jun. 17-19, 2009, Symposium, workshop & Poster Session, p. 74.*
H. Li, S. Yang, B. Mu, Z. Rong, J. Zhang, Molecular phylogenetic diversity of the microbial community associated with a high-temperature petroleum reservoir at an offshore oilfield, FEMS Microbiol Ecol, 2007, 60, 74-84.*
G. T. de Acevedo, M.J. McInerney,Emulsifying activity in thermophilic and extremely thermophilic microorganisms, Journal of Industrial Microbiology, 1996, 16, 1-7.*
N. Youssef, M. S. Elshahed, M. J. McInerney, Microbial processes in oil fields: culprits, problems, and opportunities, Advances in applied microbiology, vol. 66, Burlington: Academic Press, 2009, pp. 141-251, Chapter 6.*
BACMAP genome atlas, downloaded Jan. 31, 2014.*
S. P. Mathupala, J. G. Zeikus, Improved purification and biochemical characterization of extracellular amylopullulanase from *Thermoanaerobacter ethanolicus* 39E, Appl Microbiol Biotechnol, 1993, 39, 487-493.*
PEMEX, Annual Report, 2009, Petroleos Mexicanos.

(Continued)

*Primary Examiner* — Susannah Chung
*Assistant Examiner* — Kumar R Bhushan
(74) *Attorney, Agent, or Firm* — Roylance, Abrams, Berdo & Goodman, L.L.P.

(57) ABSTRACT

A process for increasing recovery of heavy oil with an API gravity equal to or greater than 10, contained in carbonate and/or sandstone porous media using extremophile (thermophilic, halotolerant and barotolerant) anaerobic indigenous microorganisms. The process involves nutrient injection to stimulate activity of extremophile anaerobic indigenous microorganisms at the well bottom, promoting the production of metabolites which improve oil mobility and increase oil recovery. Stimulation of extremophile anaerobic indigenous microorganisms and their metabolite production is conducted under anaerobic conditions at temperatures of 45 to 90° C., NaCl concentrations of 5,000 to 40,000 mg/L and pressures of 0.795 to 169 Kg/cm$^2$ (11.3 to 2,400 psi). Heavy oils are recovered with API gravity equal to or greater than 10 degrees. The process enables up to 21% oil recovery in addition to the waterflooding process in porous media.

14 Claims, 4 Drawing Sheets

(56) References Cited

OTHER PUBLICATIONS

Sen, R., Biotechnology in petroleum recovery: The microbial EOR, Progress in Energy and Combustion Science, 34 (2008) 714-724.
Sandrea, I. et al., Global Oil Reserves—Recovery Factors Leave Vast Target for EOR Technologies, Oil & Gas Journal, 2007, pp. 1-8.
Bryant, R. et al., Biotechnology for heavy oil recovery, 7th UNITAR International Conference on Heavy Crude and Tar Sands, 1998.
Wankui, G. et al., Microbe-enhanced oil recovery technology obtains huge success in low-permeability reservoirs in Daqing oilfield, SPE: Eastern Regional Meeting, 2006, pp. 45-52.

* cited by examiner

HEAVY OIL RECOVERY PROCESS USING EXTREMOPHILE ANAEROBIC INDIGENOUS MICROORGANISMS

CROSS-REFERENCE TO RELATED APPLICATION

Reference is made to commonly-owned U.S. application Ser. No. 12/973,258, filed Dec. 20, 2010, of Patricia Olguin Lora et al., entitled "Biotechnological Process for Hydrocarbon Recovery in Low Permeability Porous Media".

FIELD OF THE INVENTION

The present invention relates to a process that increases the heavy oil recovery with an API gravity equal to or greater than 10 degrees, contained in carbonate and/or sandstone porous media, by nutrient injection in order to stimulate activity of extremophile anaerobic indigenous microorganisms in the well bottom to promote the metabolites production; these microorganisms grow under anaerobic conditions at pressures of 0.795 to 169 $Kg/cm^2$ (11.3 to 2,400 psi), temperatures of 45 to 90° C., and NaCl concentration of 5,000 to 40,000 mg/L, and are capable of increasing the oil mobility and recovery.

BACKGROUND

Heavy oils as an energy resource represents more than half world's oil resources, according to the International Energy Agency (World Energy Outlook 2008). In this regard, it is important to note that the American Petroleum Institute classifies heavy oil as having an API gravity between 10 and 22.3.

The demand for heavy oil has been marginal, due to high viscosity and complexity of its composition, which makes its production or recovery from the reservoir difficult. To meet the demand of light crude oil, which is currently in decline, increased production of heavy and extra-heavy oils could be carried out in several regions such as the Gulf of Mexico and North-eastern China. Table 1 shows the heavy oil reserves in Mexico (Annual Report 2009, Petróleos Mexicanos, Pemex), which shows that more than half of proven reserves in Mexico are of heavy oils.

TABLE 1

Heavy oil reserves in Mexico (Annual Report, Pemex 2009)

| Reserve type | Million barrels | Heavy oil (%) |
| --- | --- | --- |
| Proven | 10,404.2 | 61.3 |
| Probable | 10,375.8 | 52.1 |
| Possible | 10,149.8 | 49.8 |

Reservoir production starts when oil flow occurs naturally to the surface (primary recovery), and then is complemented by waterflooding or gas injection as secondary recovery processes. After these steps, tertiary or enhanced oil recovery (EOR) procedures are applied. The EOR process consists of injection of: miscible solvent, hydrocarbon gases or carbon dioxide, soda water, surfactants or soluble polymers, and biological products to reservoirs, and steam-assisted gravity. These processes include any methods to provide an energy source to the reservoir and to maximize the economic value of hydrocarbon reserves (Sen R., 2008: Biotechnology in petroleum recovery: The microbial EOR. Progress in Energy and Combustion Science. 34:714-724).

Primary recovery of heavy oils is reported as 10 to 15%, secondary recovery as 20-25% and enhanced oil recovery processes as 2-6% (Sandrea I. and Sandrea R., 2007: Global Oil Reserves—Recovery Factors Leave Vast Target for EOR Technologies. Oil & Gas Journal. Part 1, November 5 and Part 2, November 12; p 1-8).

Physicochemical EOR processes demand high energy consumption, which represents a high cost; and are not compatible with the environment. Therefore it is important to develop alternative technologies to improve heavy and extra heavy oil recovery from reservoirs. Some of these alternative technologies are related to microbial recovery methods, which represent a low-cost alternative and are environmentally compatible. Microorganisms produce a variety of products (gases, biosurfactants, biopolymers and solvents), which can reduce oil viscosity, change rock wettability, reduce interfacial tension and form stable oil-water emulsions; and also modify the oil properties, and thus increase the oil recovery in the reservoir (Bryant et al., 1998: Biotechnology for heavy oil recovery. 7th UNITAR International conference on heavy crude and tar sands).

In Mexican Patent Application No. MX/a/2009/014146, "Biotechnological process for hydrocarbon recovery in low permeability porous media", filed Dec. 21, 2009, Olguín-Lora et al., refer a biotechnological process that increases recovery of oil with API gravity of 14 to 25 degrees, by stimulating the activity of extremophile indigenous microorganisms in the reservoir, capable of growing under anaerobic conditions at temperatures from 60 to 95° C., and pressures of 7 to 154.6 $Kg/cm^2$ (100 to 2,200 psi). The described process can recover 11 to 30% oil, in addition to a secondary recovery process in porous media. This invention was not developed for recovery of oils with less than 14° API, temperatures below 60° C. and pressures greater than 154.6 $Kg/cm^2$ (2,200 psi).

In Patent application WO 2009/009382 A3 "Process for enhanced oil recovery using a microbial consortium", published on Jan. 15, 2009, Soni et al. describe a microbial method for recovering oil from naturally fractured sandstone or carbonate formations, with rock porosity >20% and reservoir temperature <90° C. This process is used for medium/light oils with viscosity <20 cp and API gravity >20°. During the process implementation, one stage is the shutdown of the well for a period of three weeks for the growth of microbial consortium, allowing microorganisms to release oil from the rock and increase recovery.

In Patent application WO 2009/001098 A3 "Method of enhancing oil recovery", published on Dec. 3, 2008, Kotlar proposes a microbial oil recovery method, with heavy oil of 10 to 22° API. The method is based on microorganism injection isolated from the indigenous population of an oil reservoir, bitumen, or volcanic sludge. These microorganisms are incubated at temperatures from 70 to 100° C. The oil treated with microorganisms reduced the viscosity from 417 to 130 cp. This invention reached oil recovery up to 66% in columns packed with granulates, which are highly permeable systems.

In Patent application US 20070092930 A1 "Process for enhanced recovery of crude oil from oil wells using novel microbial consortium" published on Apr. 26, 2009, Lal et al. describe a process for oil recovery, using a mixed culture of thermophilic, acidogenic, barophiles and anaerobic bacteria, grown in a culture medium containing nutrients, minerals and a complex carbon source at temperatures from 70 to 90° C. Recovery examples of this invention were performed on columns packed with sand and residual saturation of 27.9%, obtaining an oil recovery of 8.9% due to microbial activity, but the examples do not show values for viscosity and API gravity of used oil.

In Patent application US 20070181300 A1 "System and method for preparing near-surface heavy oil for extraction using microbial degradation", published on Aug. 9, 2007, Bushe and Rollins propose a heavy oil recovery system by using bacteria and fungi, with a nutrient addition. The field application is focused on hydrocarbons located near to reservoir surfaces, which means that the invention is used at relatively low temperatures and surface pressures. The authors describe only the recovery process, without providing information about oil and formation types, where the method can be applied.

Wankui et al., 2006: Microbe-enhanced oil recovery technology obtains huge success in low-permeability reservoirs in Daqing oilfield. SPE: Eastern Regional Meeting 2006, p. 45-52, 2006, describe the application on field of a biological process based on the injection of microorganisms in reservoirs. They report that injected microorganisms are adapted to reservoir conditions, degrade heavy oil, improve oil characteristics and produce biosurfactants, increasing oil production of 24.7 ton/d (before microorganism injection) to 40.8 ton/d. The authors did not provide information about viscosity and API gravity of oil recovered.

In the cited references, oil recovery using microorganisms has been carried out mainly in granular systems, sand-packed columns and, in some cases, low permeability porous media. Most of these references do not indicate the pressure condition to which they apply oil recovery processes; neither provides important characteristics of the oil such as viscosity and API gravity.

It is also important to note that the references described do not provide examples for conditions of greater than 2,200 psi pressure or recovery of heavy oil with API gravity <14 in consolidated systems such as cores; although there are recovery reports using microorganisms in columns, using heavy oils. These systems have higher permeability and porosity, and therefore are not comparable to consolidated systems. Thus, it is important to have processes that can be applied to carbonate and/or sandstone reservoirs and heavy oils to 10° API, where the nutrients and/or microorganisms are injected; and that include a well closure for a period of at least 7 days, less than reported in other patents.

SUMMARY OF THE INVENTION

A biotechnological recovery process has now been found for heavy oil having an API gravity equal or greater than 10 degrees from porous media in an oil well that comprises the following steps:
a) Selecting an oil well for recovery of heavy oil;
b) Collecting one or more fluid samples from the oil well and performing microbiological and physicochemical characterization of the fluid samples to obtain technical information on the well;
c) Determining the identity of extremophile anerobic indigenous microorganisms present in the well from the technical information;
d) Forming a culture medium, suitable for stimulating activity and promoting production of metabolites by the extremophile anaerobic indigenous microorganisms in the well;
e) Forming a mixed culture of microorganisms comprising the microorganisms from the samples of steps b) and c) which are extremophile, anerobic indigenous microorganisms of the well and the fermentative and methanogenic anaerobic, thermophilic, halotolerant and barotolerant microorganisms *Thermoanaerobacter pseudoethanolicus, Thermoanaerobacter brockii, Thermoanaerobacter keratinophilus* and *Methanobacterium thermoautotrophicus*;
f) Injecting an inoculum comprising the culture medium of step d) and the mixed culture of e) into the well to increase the population of indigenous microorganisms in the well;
g) Recovering heavy oil from the well after a minimum of 3 days after the injection of the microorganisms and nutrients.

In this regard, the present invention provides a process that increases the recovery of heavy oil with API gravity equal to or greater than 10 degrees, contained in carbonate and/or sandstone porous media, preferably in oil wells with low-productivity, using extremophile anaerobic indigenous microorganisms.

The process of the present invention is based on nutrient injection to stimulate the activity of extremophile anaerobic indigenous microorganisms in the well bottom to promote metabolites production, which increases oil mobility and facilitates its recovery.

In the present invention, microbial activity stimulation of extremophile anaerobic indigenous microorganisms, and production of their metabolites are carried out under anaerobic conditions at temperatures from 45 to 90° C., NaCl concentrations of 5,000 to 40,000 mg/L and pressures of 0.795 to 169 Kg/cm$^2$ (11.3 to 2,400 psi).

DETAILED DESCRIPTION OF THE INVENTION

The present invention relates to a process that increases the recovery of heavy oil with API gravity equal to or greater than 10 degrees, contained in carbonate and/or sandstone porous media, using anaerobic indigenous extremophile microorganisms; thermophilic, halotolerant and barotolerant, at temperatures of 45 to 90° C., pressures of 0.795 to 169 Kg/cm$^2$ (11.3 to 2,400 psi) and NaCl concentrations of 5,000 to 40,000 mg/L.

The process of the present invention is based on nutrient injection to the well bottom in order to stimulate the activity of anaerobic extremophile indigenous microorganisms to promote the production of metabolites, which increases the oil mobility and facilitates the recovery.

The present invention provides a mixed culture that produces metabolites, gases such as $CO_2$, $CH_4$ and $H_2$, biosurfactants, acids (acetic, propionic and butyric acids), and solvents (ethanol and acetone), which help the recovery of heavy oil with API gravity equal to or greater than 10 degrees by mechanisms such as pressurization, dissolution, emulsification, interfacial tension reduction and viscosity reduction.

Figure 1:
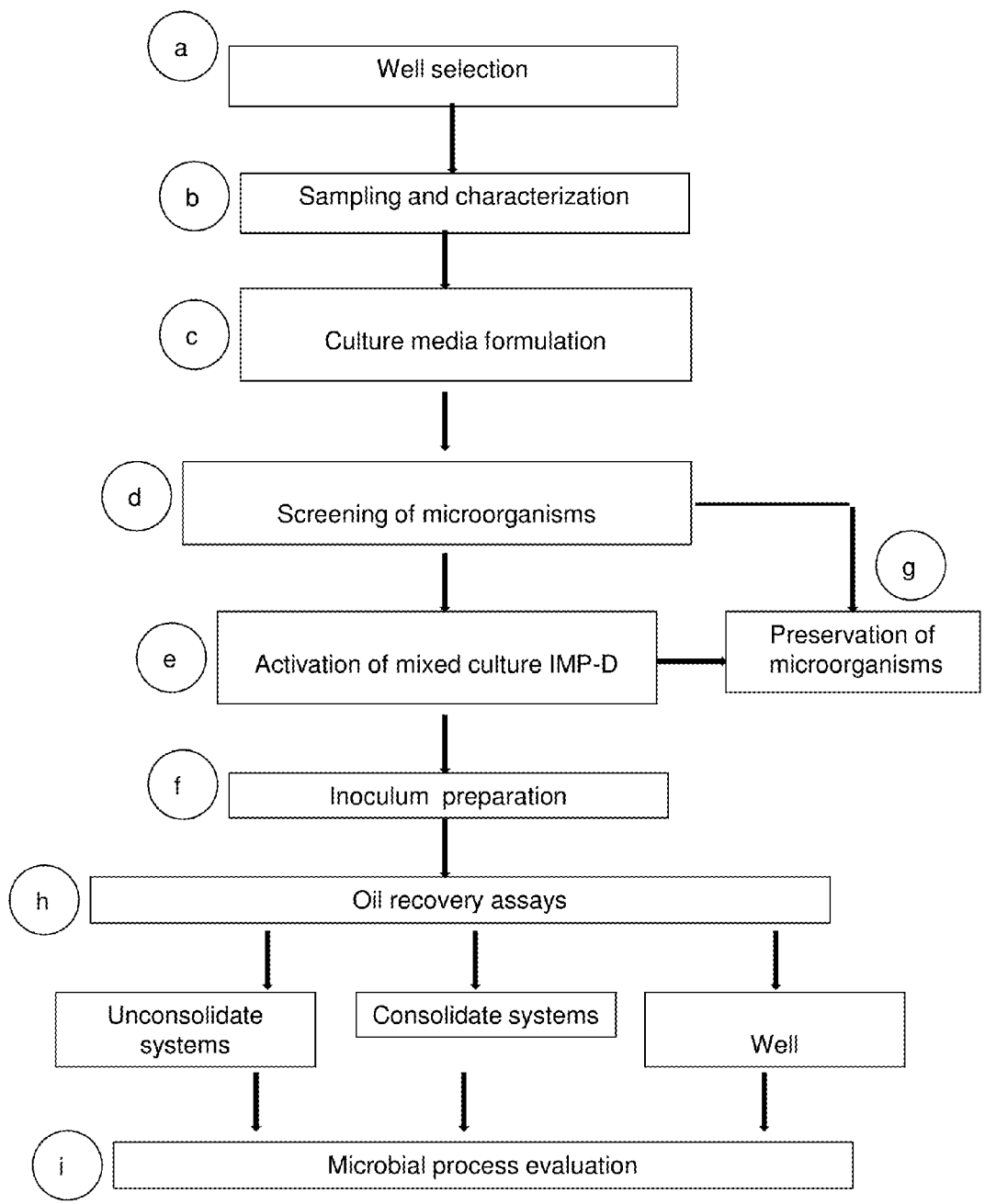
FIG. 1 shows a flow diagram with the different steps involved in the biotechnological process of the present invention for the heavy oil recovery from porous media by using extremophile anaerobic indigenous microorganisms.

The present invention describes a process to recover heavy hydrocarbons, which have API gravity equal to or greater than 10 degrees, with a recovery factor up to 21% additional to oil secondary recovery process in porous media. To have a better understanding of the biotechnological process disclosed herein for the recovery of heavy hydrocarbons in a porous medium by using extremophile anaerobic indigenous microorganisms, FIG. 1 shows a flow diagram with the different steps involved:

a) Oil well selection. From oil field information, select the well for heavy oil recovery by using extremophile anaerobic indigenous, considering the following conditions:
   Formation type: carbonated and/or sandstone;
   Reservoir temperature: 45 to 90° C.;
   Reservoir pressure: 0.795 to 169 Kg/cm$^2$ (11.3 to 2,400 psi); and
   Salinity of formation water: 5,000 to 40,000 mg/L as NaCl.

b) Sampling and characterization. Involves collecting samples of oil well and/or reservoir: rock, oil and formation water, as well as information relating thereto. Fluid samples collected are physicochemically and microbiologically characterized. Compiled information includes oil data such as: API gravity, density, viscosity, acidity, salinity, pH; and petrophysical rock data such as porosity, permeability, rock type and reservoir temperature, production data, well pressure and temperature.

c) Formulation of culture media. It is necessary to stimulate the activity of extremophile anaerobic indigenous microorganisms downhole, and promote the production of useful metabolites to increase heavy oil recovery with thermophilic, halotolerant and barotolerant anaerobic mixed culture at temperatures from 45 to 90° C., pressures of 0.795 to 169 Kg/cm$^2$ (11.3 to 2,400 psi), and NaCl content of 5,000 to 40,000 mg/L. Tables 2 to 5 show the culture media composition for growth of microorganisms.

TABLE 2

Culture medium composition for fermentative microorganisms

| Compound | Formula | Concentration (g/L) |
|---|---|---|
| Ammonium chloride | $NH_4Cl$ | 0.2-0.5 |
| Magnesium chloride | $MgCl_2 \cdot 6H_2O$ | 1.0-1.5 |
| Dibasic potassium phosphate | $K_2HPO_4$ | 0.1-0.3 |
| Potassium chloride | KCl | 0.3-0.5 |
| Calcium chloride | $CaCl_2 \cdot 2H_2O$ | 0.1-0.2 |
| Casein peptone | | 1.0-3.0 |
| Yeast extract | | 1.0-3.0 |
| Sodium chloride | NaCl | 5-40 |
| Carbon source: Molasses | | 2-10 |
| Sodium bicarbonate | $NaHCO_3$ | 0.5-1.0 |
| Sodium sulfide | $Na_2S$ | 0.1-0.2 |
| Cysteine-HCl | | 0.1-0.3 |

TABLE 3

Culture medium composition for methanogenic archaea

| Compound | Formula | Concentration (g/L) |
|---|---|---|
| Potassium chloride | KCl | 0.2-0.5 |
| Magnesium chloride | $MgCl_2 \cdot 6H_2O$ | 3-5 |
| Ammonium chloride | $NH_4Cl$ | 0.2-0.4 |
| Calcium chloride | $CaCl_2 \cdot 2H_2O$ | 0.1-0.3 |
| Dibasic potassium phosphate | $K_2HPO_4$ | 0.1-0.3 |
| Calcium chloride | NaCl | 5-30 |
| Sodium carbonate | $Na_2CO_3$ | 5-10 |
| Sodium acetate | $CH_3COONa$ | 0.5-2 |
| Yeast extract | | 1-4 |
| Trypticase | | 1-4 |
| Sodium Sulfide | $Na_2S \cdot 9H_2O$ | 0.2-0.6 |
| Trace elements solution[1] | | 5-10 mL |
| Vitamins solution[1] | | 5-10 mL |

[1]The composition for trace elements solution and vitamins solution are presented in Table 4 and Table 5, respectively.

TABLE 4

Trace elements solution of culture media for methanogenic archaea

| Compound | Formula | Concentration (g/L) |
|---|---|---|
| Nitrilotriacetic acid | $C_6H_9NO_6N \cdot (CH_2COOH)_3$ | 1-2 |
| Manganese (II) sulfate dihydrate | $MnSO_4 \cdot 2H_2O$ | 0.2-0.6 |
| Sodium chloride | NaCl | 0.5-2 |
| Iron (II) sulfate heptahydrate | $FeSO_4 \cdot 7H_2O$ | 0.05-0.2 |
| Cobalt (II) sulfate heptahydrate | $CoSO_4 \cdot 7H_2O$ | 0.1-0.3 |
| Calcium chloride dihydrate | $CaCl_2 \cdot 2H_2O$ | 0.1-0.2 |
| Zinc sulfate heptahydrate | $ZnSO_4 \cdot 7H_2O$ | 0.1-0.2 |
| Copper (II) sulfate pentahydrate | $CuSO_4 \cdot 5H_2O$ | 0.01-0.1 |
| Boric acid | $H_3BO_3$ | 0.01-0.1 |
| Sodium molybdate dihydrate | $Na_2MoO_4 \cdot 2H_2O$ | 0.01-0.1 |
| Nickel (II) chloride hexahydrate | $NiCl_2 \cdot 6H_2O$ | 0.02-0.1 |
| Sodium selenite pentahydrate | $Na_2SeO_3 \cdot 5H_2O$ | 0.20-0.5 mg |

TABLE 5

Vitamins solution of culture media for methanogenic archaea

| Compound | Concentration (mg/L) |
|---|---|
| Biotin | 1-5 |
| Folic Acid | 1-5 |
| Pyridoxine-HCl | 7-12 |
| Thiamin-HCl | 4-8 |
| Riboflavin | 3-6 |
| Nicotinic acid | 3-6 |
| Calcium pantothenate | 3-6 |
| $B_{12}$ Vitamin | 0.1-0.3 |
| p-Aminobenzoic acid | 3-6 |
| Lipoic acid | 3-6 | d) Screening of microorganisms. This section is focused on growth of fermentative and methanogenic anaerobic, thermophilic, halotolerant and barotolerant microorganisms, which grow and are active under the described conditions in step a), isolated from oil samples of oil wells. The mixed cultures of extremophile anaerobic fermentative and methanogenic microorganisms are obtained from oil samples of oil wells, using enrichment cultures with nutrient composition described in step c).

e) Activation of mixed culture IMP-D. Consist in the stimulation and growth of the mixed culture IMP-D by using the culture media described in table 2, step c). Mixed culture IMP-D is constituted of extremophile anaerobic indigenous microorganisms and dominated by the following: *Thermoanaerobacter pseudoethanolicus, Thermoanaerobacter brockii, Thermoanaerobacter keratinophilus* and *Methanobacterium thermoautotrophicus*. This culture is adapted to the following well conditions: temperature 45 to 90° C.; preferably 55 to 75° C., salinity from 5,000 to 40,000 mg/L of NaCl, and pressure of 0.795 to 169 kg/cm$^2$ (11.3 to 2,400 psi); and it grows in the presence of oils with API gravity equal to or greater than 10 degrees.

In order to confirm the ability of microorganisms to produce useful metabolites for oil recovery, the rate of growth of microbial culture was evaluated at temperature, pressure and salinity of the well.

f) Preparation of inoculum for heavy oil recovery. The present invention provides a process where the inoculum is comprised of extremophile anaerobic indigenous microorganisms from Mexican oil wells and mixed culture IMP-D, with microorganisms mentioned in steps d) and e).

g) Preservation of microorganisms from oil wells. Preservation of extremophile anaerobic microorganisms from steps d), e) and f) is performed by fixing on an inert support, such as paper and/or sand, under sterile conditions to preserve and maintain their viability.

h) Heavy oil recovery assays in porous media. They consist of recovery assays with an injection of microorganisms from steps d), e) and f) which are adapted to oil well temperature, pressure and salinity conditions; and a nutrient injection described in table 2, step c) necessary for microbial growth and metabolite production, useful in heavy oil recovery in the following porous media:

Unconsolidated systems. It involves the addition of microbial mixed culture from steps d), e) and f), and the culture medium described in table 2, step c) to a porous medium saturated with oil and the recovery evaluation (Example 2);

Core systems. It involves the addition of microbial mixed culture from steps d), e), and f) and the culture medium described in table 2, step c) to carbonates and/or sandstone core saturated with oil and confined for a period of less than 7 days; preferably 3 to 7 days, allowing growth and useful metabolites production for oil recovery (Examples 3 to 5).

Oil well. It consists of a process implementation disclosed herein in an oil well to increase heavy oil recovery.

i) Evaluation of microbial process. Determination of heavy oil recovery percentage due to biological process. Evaluate the effect of microorganisms on recovered oil, by analysis of SARA fractions (saturates, aromatics, resins, and asphaltenes), hydrocarbon distribution, oil viscosity, and metabolites production ($CO_2$, acids, solvents and biosurfactants).

Finally, the addition of nutrients and extremophile anaerobic microorganisms is done in one or more cycles with short confinement periods of less than 7 days—preferably 3 to 7 days.

EXAMPLES

Some practical examples of the present invention are following stated for a better understanding, not limiting its scope.

Example 1

Microbial Activity of Mixed Culture IMP-D

Growth and metabolites production of mixed culture IMP-D were evaluated. Mixed culture IMP-D was isolated from crude oil samples from a Mexican oil well, using the nutrients described in table 2, step c) of the biotechnological process disclosed herein, at the following conditions: temperatures of 45 to 90° C., pressures of 0.795 to 169 Kg/cm$^2$ (11.3 to 2,400 psi), NaCl concentration of 5,000 to 40,000 mg/L and molasses as carbon source of 0.5 to 11 g/L. The results are shown in FIGS. 2 and 3.

Figure 2:
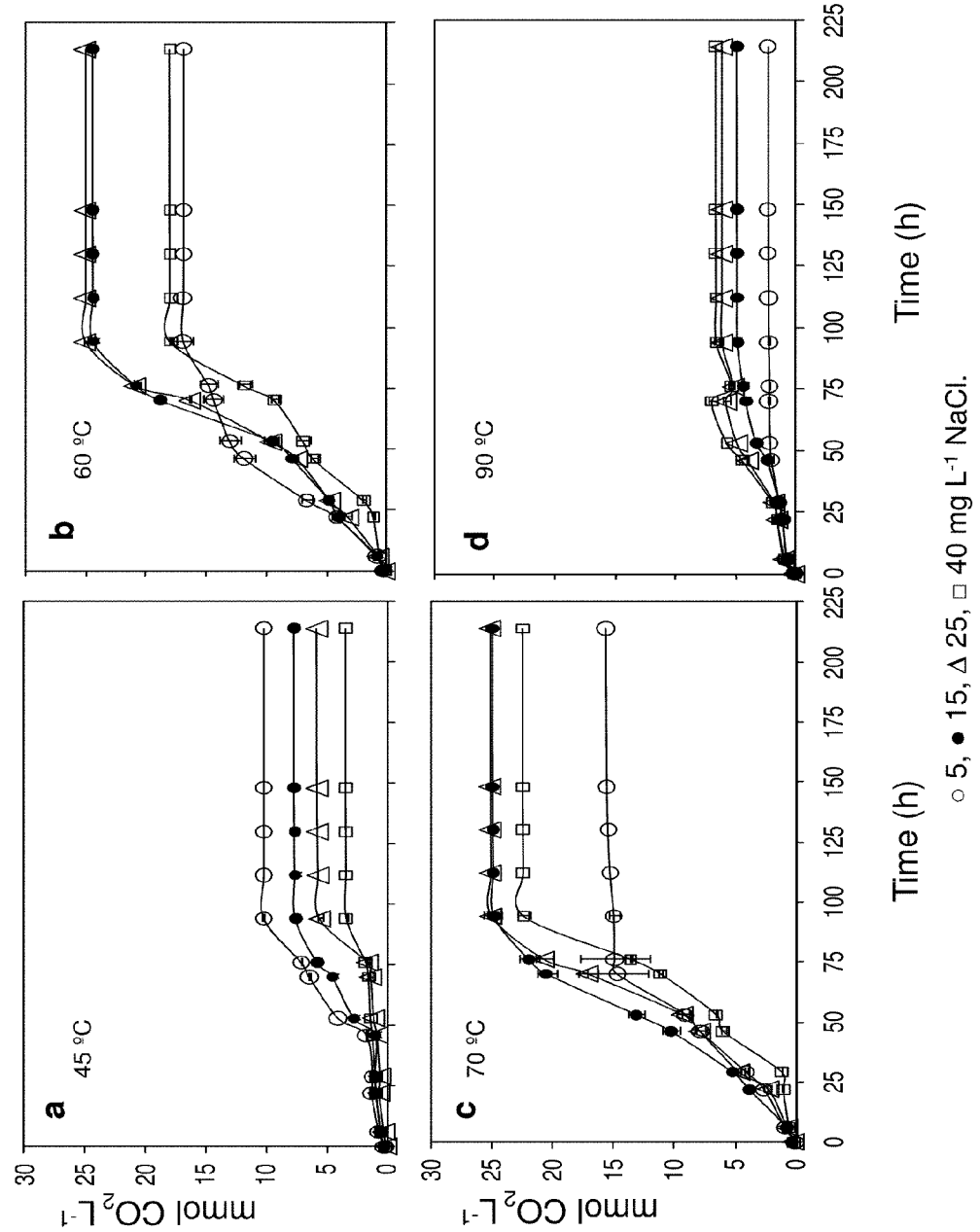
FIG. 2 shows $CO_2$ production by mixed culture IMP-D at different temperatures and NaCl concentrations.
Figure 3:
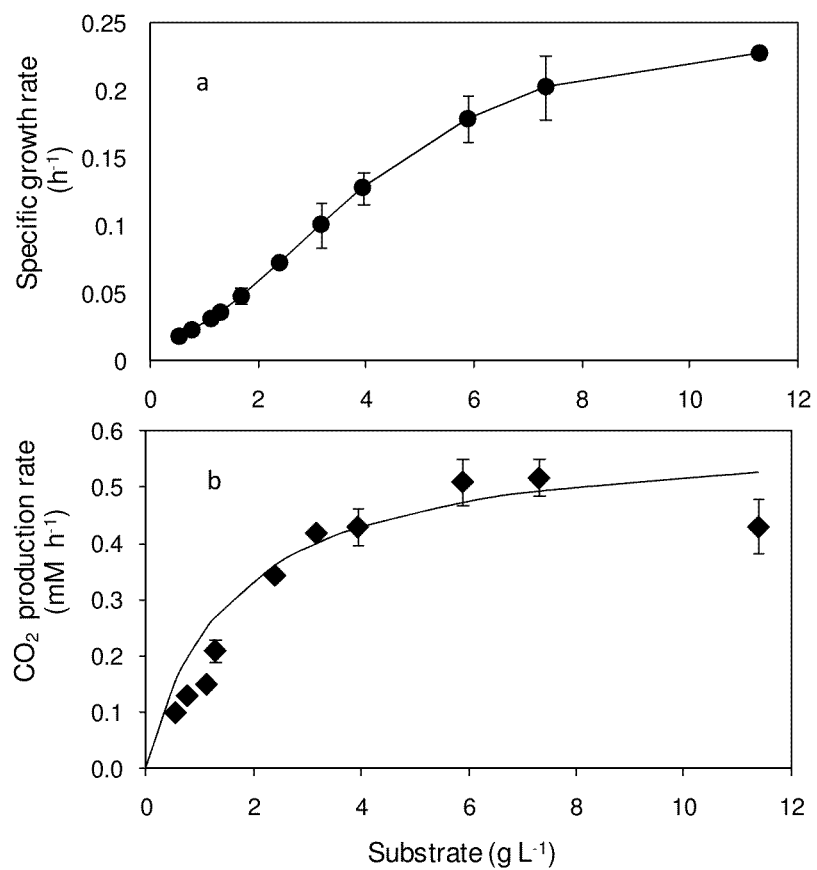
FIG. 3 shows the specific growth rate and $CO_2$ production rate of mixed culture IMP-D at different molasses concentrations.

FIGS. 2 and 3 show that microorganisms present in mixed culture IMP-D were able to grow at conditions indicated in previous paragraph, but preferably at temperatures from 55 to 75° C.

Example 2

Recovery Test by Microorganisms in Unconsolidated Systems Saturated with Heavy Oil, API Gravity Equal to or Greater than 10 Degrees To evaluate the effect of microorganisms on oil recovery from porous media; carbonated and sandstone rocks with particle size of 0.29 to 0.42 mm were used. Oil saturation under a vacuum of unconsolidated systems, using Mexican heavy oil with API gravity equal to and greater than 10 degrees, was performed. Systems were added with culture media listed in Tables 2 to 5 and an inoculum consisting of mixed culture IMP-D, containing microorganisms indicated in step e) and microorganisms obtained from crude oil samples indicated in step f) of the bioprocess description disclosed herein. Systems were incubated at 45 to 90° C., under anaerobic conditions for 15 to 22 days.

Production of $CO_2$, ethanol and acetic acid in all systems was detected. Production of these metabolites is favourable because of their effect on fluid properties in porous media.

The net recovery of heavy oil, with API gravity equal to or greater than 10 degrees attributed to microbial activity, was 10.4% ±0.85, for both rocks types (Table 6).

TABLE 6

Recovery assay conditions in unconsolidated granular porous media.

| Conditions | Test 1 | Test 2 |
| --- | --- | --- |
| Microbial culture | IMP-D | IMP-D |
| Rock type | Carbonate | Sandstone |
| Particle size, mm | 0.29-0.42 | 0.29-0.42 |
| Oil | Heavy oil | Heavy oil |
| API gravity, degrees | 10-14 | 10-14 |
| Viscosity at 70° C., cp | 631.5 | 631.5 |
| Salinity, % NaCl | 5-35 | 5-35 |
| Temperature, ° C. | 45-90 | 45-90 |
| Pressure, psi | 11.3 | 11.3 |
| Initial oil saturation, % | 100 | 100 |
| Oil recovery by micoorganisms, % | 10.2 | 12 |
| Detected metabolites: | | |
| Acetic acid, mg/L | 560 | 380 |
| Ethanol, mg/L | 2,060 | 1,350 |
| $CO_2$, mmol/L | 23.2 | 18.5 |
| Biomass, mg/L | 518.5 | 395.7 |

Example 3

Figure 4:
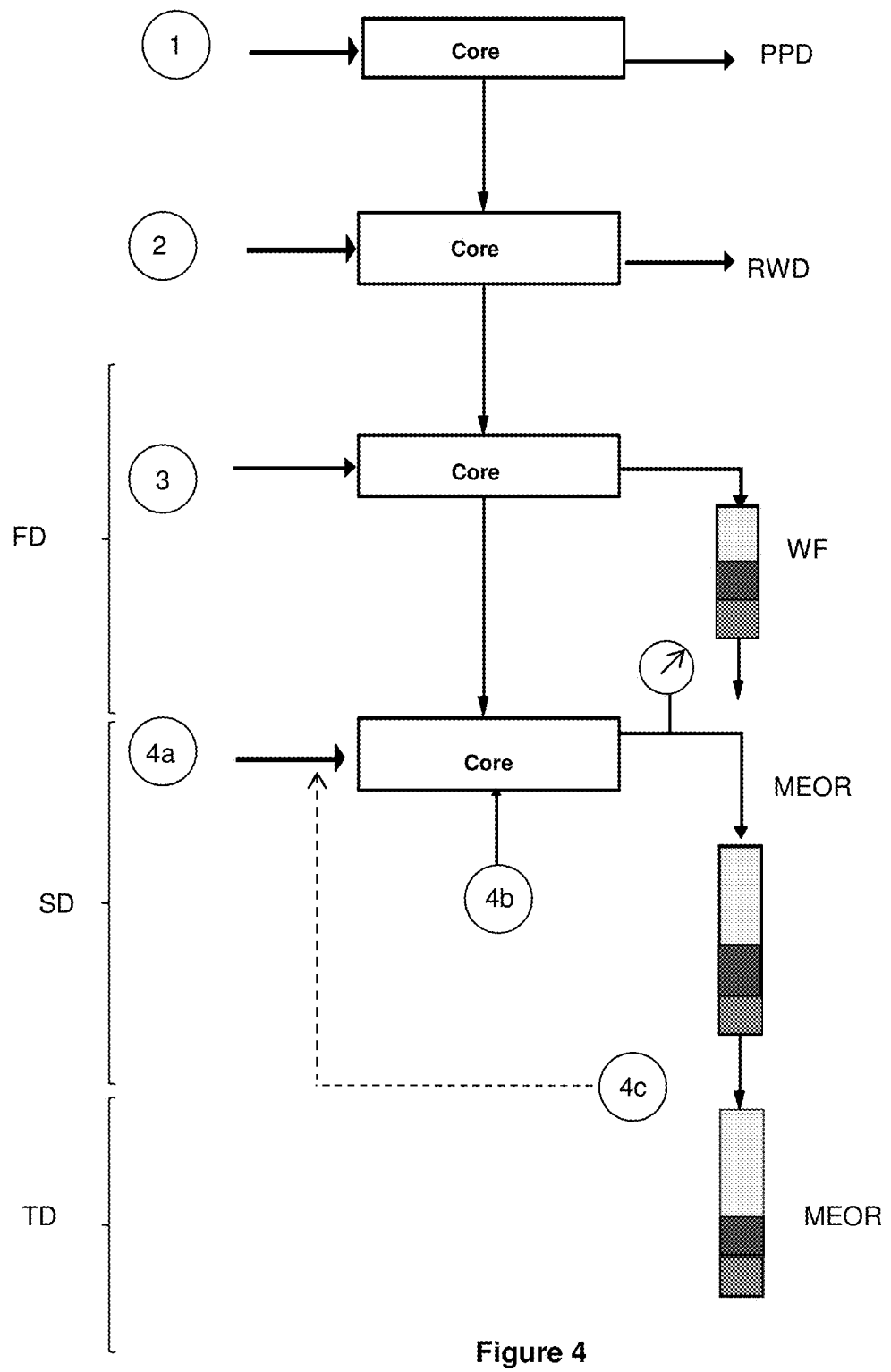
FIG. 4 shows a general diagram of heavy oil recovery test in porous media by injection of nutrients and extremophile anaerobic indigenous microorganisms.

Recovery Test by Microorganism Injection in Consolidated Systems Saturated with Heavy Oil, API Gravity Equal to or Greater than 10 Degrees FIG. 4 shows a general flow diagram for a heavy oil recovery test by injection of microorganisms and nutrients in a porous media. For this particular case, sandstones porous media was used. The overall strategy is divided into several steps:

1) Brine injection for porous medium (core) saturation and porosity and permeability determination (PPD) on the output.

2) Oil injection for system (core) saturation and residual water determination (RWD) on the output.
3) Brine injection to the core, waterflooding (WF), corresponding to the first displacement (FD).
4) Start of oil recovery by microorganisms indicated in step f), corresponding to second displacement (SD) that includes:
   a. Injection of culture medium or nutrients and microorganisms to the core;
   b. Core confinement: incubation in static conditions at 45-90° C. for 3 to 7 days; and
   c. Injection of culture medium or nutrients and microorganisms to the core, corresponding to third displacement (TD), which includes: oil recovery by effect of microorganisms and their metabolites, microbial enhanced oil recovery (MEOR).

Sandstone core dimensions used in the experimental cell of the oil recovery test were 10.16 cm diameter and 13.0 cm length.

The oil recovery experimental system consisted of: core container cells, controlled pressure injection pumps, oven, pressure measurement systems and pressure regulators.

To take advantage of fluid density in both saturation and recovery steps, the core container cell was placed in a vertical arrangement. The cell was placed inside an oven for temperature control at 45-90° C. Transfer cylinders were used to displace fluids (brine, oil and inoculum) through the core. A differential transducer was installed to record pressure drop in the development of the experimental test. A gas sampling and recovery system, as well as a recovered fluid collection system at the output of experimental cell, were installed.

Brine with 5,000 to 40,000 mg/L of NaCl was displaced through the core at an injection flow of 2.5-10 mL/h. To achieve saturation, 1.5 to 3.0 pore volumes of brine was injected. The sandstone core was saturated with Mexican heavy oils of API gravity equal to or greater than 10 degrees. 1.5-3.0 porous volumes of oil were injected at a flow of 2.5-10 mL/h, and volumes of recovered brine and residual oil in core were measured.

All recovery steps were conducted under controlled conditions at pressures of 5.6 to 169 Kg/cm$^2$ (80 to 2.400 psi), temperatures of 45-90° C. and in an anaerobic environment, allowing the system stabilization to these conditions.

Waterflooding with Brine Injection (WF)

Oil secondary recovery was carried out by injecting brine (5.000 to 40.000 mg/L of NaCl) at 2.5-10 mL/h rate and 45-90° C. (FIG. 4, FD). The recovery was completed when brine and no more released oil in the effluent were detected.

Microbial Enhanced Oil Recovery (MEOR)

After completion of the waterflooding process, the mineral medium (Tables 2 to 5) was injected with molasses (5-10 g glucose/L), mixed culture inoculum IMP-D and microorganisms extracted from oil well samples as indicated in step f) of the biotechnological process description of the present invention. The inoculum was injected at 2.5-10 mL/h rate, reaching about 1.5-3.0 of volumes porous.

Confinement Step

Once the core was saturated with culture media and microorganisms, the injection was stopped and the system was confined to 45-90° C. for 3-7 days. During this period, the microorganisms grew and produced metabolites that are useful for improving oil mobility and hence oil recovery.

After a confinement period of 3 to 7 days, the system was opened; culture media and inoculum were again injected. The oil recovery was evaluated. Gas production during the test was determined and aqueous effluent recovered, and the production of other metabolites (biosurfactants, acids and solvents) was evaluated.

Conditions and materials used in this test are shown in Table 7.

TABLE 7

Conditions of oil recovery test in consolidated porous media.

| Characterictic/Conditions | Example 3 | Example 5 |
|---|---|---|
| Microbial culture | IMP-D | IMP-D |
| Oil type | Heavy oil | Heavy oil |
| API gravity, degrees | 10-14 | 10-14 |
| Viscosity at 70° C., cp | 631.5 | 631.5 |
| Brine, % NaCl | 5-35 | 5-35 |
| Formation type | Sandstone | Carbonate |
| Temperature, ° C. | 45-90 | 45-90 |
| Pressure, psi | 80-2,400 | 80-2,400 |
| Pore volume, m$^3$ | 215-226 | 49.5 |
| Porosity, % | 19-22 | 18.0 |
| Flow, mL/h | 5-10 | 5-10 |
| Initial oil saturation, % | 74-76 | 84.8 |
| Water saturation, % | 19.8 | 15.2 |
| Recovery by waterflooding (brine injection), % | 49.45 | 34.3 |
| Recovery by the invention (with microorganisms, MEOR), % | 8.8-10.5 | 20.7 |
| Total recovery (waterflooding and MEOR), % | 58.3-59.95 | 55.0 |
| Residual oil recovery (additional waterflooding), % | 19.48-21 | 31.5 |
| Detected metabolites | Acids, gas, solvents, biomass | Acids, gas, solvents, biomass |

In this Example:
- A recovery of 8.8-10.5% from initial oil in the system and 19.48-21% were obtained by microbial effect after waterflooding.
- $CO_2$ production of 45% was detected only in the oil recovery phase by microorganisms.
- Acids and solvents production, also in aqueous effluent from the oil recovery phase by microorganisms, was detected, with maximum concentrations of 2,000 mg/L and 998 mg/L of ethanol and acetic acid, respectively.

Example 4

Heavy Oil Recovery Test, with API Gravity Equal to or Greater than 10 Degrees, by Microorganism Injection with Several Injection Cycles in Consolidated Systems The same conditions and materials of Example 3 were used, except the microorganism and nutrient addition, which were added more than two times with short confinement periods of 3 to 5 days. At the end of the test, a recovery of 20.93% from the initial oil was obtained, in addition to waterflooding.

Example 5

Increase of Heavy Oil Recovery by Microbial Activity in Core of Carbonate Rock

This test was performed under same conditions and with the materials and steps described in Example 3, except that the porous material used was carbonate type, as indicated in Table 7. Microorganism and culture medium injection was conducted in cycles of 1 to 3, with confinement periods of 3 to 7 days. At the end of microbial process, a total recovery of 20.7% from the initial oil in the system and 31.5% from the residual oil after secondary recovery was obtained.

Table 7 shows the conditions and results of recovery experiments of heavy oil performed in two porous media: sandstone and carbonate, using mixed microbial culture IMP-D isolated from a Mexican oil well at temperatures of 45 to 90° C., pressures of 5.6 to 169 Kg/cm$^2$ (80 to 2.400 psi), and salinities of 5,000 to 40,000 mg/L NaCl.

What is claimed is:

1. A biotechnological recovery process for heavy oil having an API gravity equal or greater than 10 degrees from porous media in an oil well that comprises the following steps:
    a) Selecting an oil well for recovery of heavy oil;
    b) Collecting one or more fluid samples from the oil well and performing microbiological and physicochemical characterization of the fluid samples to obtain technical information on the well;
    c) Determining the identity of extremophile anerobic indigenous microorganisms present in the well from the technical information;
    d) Forming a culture medium, suitable for stimulating activity and promoting production of metabolites by the extremophile anaerobic indigenous microorganisms in the well;
    e) Forming a mixed culture of microorganisms comprising the microorganisms from the samples of steps b) and c) which are extremophile, anaerobic indigenous microorganisms of the well and the fermentative and methanogenic anaerobic, thermophilic, halotolerant and barotolerant microorganisms *Thermoanaerobacter pseudoethanolicus, Thermoanaerobacter brockii, Thermoanaerobacter keratinophilus* and *Methanobacterium thermoautotrophicus;*
    f) Activation of the mixed culture obtained in step e), for stimulation and growth of microorganisms contained in mixed culture obtained from oil samples;
    g) Injecting an inoculum comprising the culture medium of step d) and the mixed culture of e) or f) into the well to increase the population of indigenous microorganisms in the well;
    h) Recovering heavy oil from the well after a minimum of 3 days after the injection of the microorganisms and nutrients.

2. A biotechnological process according to claim 1, where the heavy oil to be recovered has an API gravity of 10 degrees.

3. A biotechnological process according to claim 1, where the porous media that contains heavy oil is a carbonate and/or sandstone formation type.

4. A biotechnological process in accordance with claim 1, where the selected oil well has the following characteristics:
    Formation type: carbonate and/or sandstone;
    Reservoir temperature: 45 to 90° C.;
    Reservoir pressure: 0.795 to 169 Kg/cm$^2$ (11.3 to 2,400 psi); and
    Formation water salinity: 5,000 to 40,000 mg/L of NaCl.

5. A biotechnological process according to claim 1, where molasses is the carbon source in the culture media formulation of step d) for growth of microorganisms.

6. A biotechnological process according to claim 1, where the mixed culture of fermentative and methanogenic microorganisms and extremophile and anaerobic microorganisms from step e) are obtained from oil samples from wells, using an enrichment culture with a nutrient composition.

7. A biotechnological process according to claim 1, where the microorganisms from steps e), f) and g) are capable of growing at temperatures of 45 to 90° C., pressures of 0.795 to 169 Kg/cm$^2$ (11.3 to 2,400 psi), and NaCl contents of 5,000 to 40,000 mg/L.

8. A biotechnological process according to claim 1, where the microorganisms from steps e), f) and g) are capable of growing at temperatures of 55 to 75° C.

9. A biotechnological process according to claim 1, where the microorganisms from steps e), f) and g) are capable of producing metabolites selected from the group consisting of gases, acids, solvents and biosurfactants that are used for the recovery of oils with API gravity of 10 degrees.

10. A biotechnological process according to claim 1, where the added microorganisms to porous media or oil well are from the mixed culture of step e), which contain the following fermentative and methanogenic, thermophilic, barotolerant and halotolerant, anaerobic microorganisms: *Thermoanaerobacter pseudoethanolicus, Thermoanaerobacter brockii, Thermoanaerobacter keratinophilus* and *Methanobacterium thermoautotrophicus.*

11. A biotechnological process according to claim 1, where the extremophile, anaerobic microorganisms from steps d), e) and f) are preserved by fixing on an inert support, such as paper and/or under sterile conditions to preserve and maintain their activity.

12. A biotechnological process according to claim 1, where the injection of the inoculum is in one or more cycles with short confinement periods of less than 7 days.

13. A biotechnological process according to claim 12, wherein the cycle is 3 to 7 days.

14. A biotechnological process according to claim 1, wherein the culture media for step d) comprises NH$_4$Cl, MgCl$_2$, 2H$_2$O, K$_2$HPO$_4$, KCl, CaCl$_2$, 2H$_2$O, Casein Peptone, Yeast extract, NaCl, Molasses, NaHCO$_3$, Na$_2$S, and Cisteine HCl.

* * * * *